US005538613A

United States Patent [19]

Brumley et al.

[11] Patent Number: 5,538,613

[45] Date of Patent: Jul. 23, 1996

[54] ELECTROPHORESIS ANALYZER

[75] Inventors: Robert L. Brumley; John A. Luckey, both of Mazomanie, Wis.

[73] Assignee: GeneSys Technologies, Inc., Madison, Wis.

[21] Appl. No.: 545,219

[22] Filed: Oct. 19, 1995

Related U.S. Application Data

[63] Continuation-in-part of Ser. No. 384,240, Feb. 6, 1995, abandoned, which is a continuation of Ser. No. 143,480, Oct. 26, 1993, abandoned.

[51] Int. Cl.[6] .......... G01N 27/26; G01N 27/447

[52] U.S. Cl. .......... 204/612; 204/461; 204/456; 204/608; 204/616; 356/344

[58] Field of Search .......... 204/612, 608, 204/616, 461, 456; 356/344

[56] References Cited

U.S. PATENT DOCUMENTS

| | | | |
|---|---|---|---|
| 4,284,412 | 8/1981 | Hansen et al. | 435/7.24 |
| 4,729,947 | 3/1988 | Middendorf et al. | 435/6 |
| 4,811,218 | 3/1989 | Hunkapiller et al. | 204/461 |
| 4,870,004 | 9/1989 | Conroy et al. | 204/461 |
| 4,881,812 | 11/1989 | Ohkubo et al. | 204/612 |
| 4,885,696 | 12/1989 | Hara | 364/497 |
| 4,941,092 | 7/1990 | Hara et al. | 364/413.15 |
| 4,971,671 | 11/1990 | Slater et al. | 204/457 |
| 5,051,162 | 9/1991 | Kambara et al. | 204/612 |
| 5,062,942 | 11/1991 | Kambara et al. | 204/612 |
| 5,069,769 | 12/1991 | Fujimiya et al. | 204/461 |
| 5,091,652 | 2/1992 | Mathies et al. | 250/458.1 |
| 5,100,529 | 3/1992 | Fujii | 204/612 |
| 5,171,534 | 12/1992 | Smith et al. | 204/612 |

OTHER PUBLICATIONS

Brumley and Smith, 1990, *Nucleic Acids Research*, 19:4121–4126.

Chen, E. and Seeburg, P., 1985, "Supercoil Sequencing: A Fast and Simple Method for Sequencing Plasmid DNA," *D.N.A.* 4:165.

Maxam, A. and Gilbert W., 1970, "A New Method for Sequencing DNA," *Proc. Natl. Acad. Sci. U.S.A.*, 74:560.

Sanger F., et al., 1977, "DNA Sequencing with Chain–Terminating Inhibitors," *Proc. Natl. Acad. Sci. U.S.A.*, 74:5463.

Smith, et al., 1986, *Nature*, 321:674–679.

*Primary Examiner*—John Niebling
*Assistant Examiner*—John S. Starsiak, Jr.
*Attorney, Agent, or Firm*—DeWitt Rose & Stevens

[57] ABSTRACT

An apparatus for detecting fluorescently-labeled molecules moving in an electrophoretic separation medium. The apparatus utilizes a scanning detection system in which multiple fluorophores are efficiently and simultaneously detected using dichroic mirrors to allow simultaneous detection of fluorescently-labeled molecules in ultrathin gels labeled with several fluorophores and to permit operation at speeds ten times faster than prior art gel separations. The apparatus also utilizes a detection system where lightweight collection optics are in motion while detection optics are fixed in a remote location, thereby allowing exceptionally high-speed scanning.

22 Claims, 7 Drawing Sheets

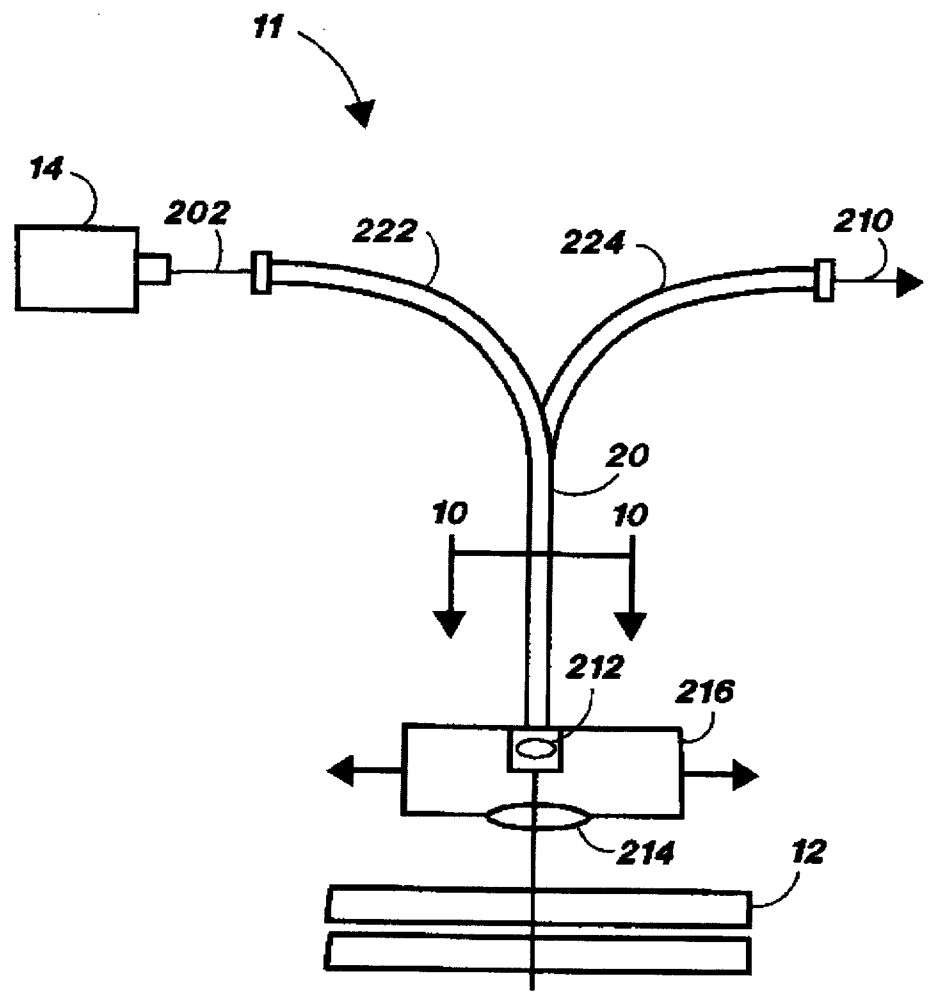
FIG. 9
FIG. 10
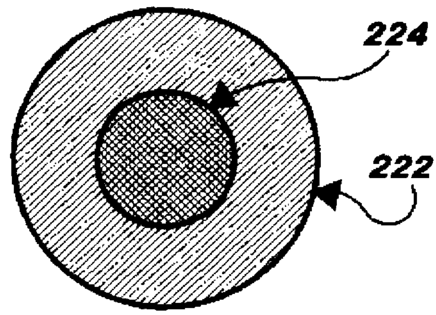
Fiber bundle

ELECTROPHORESIS ANALYZER

This application is A Continuation-In-Part of application Ser. No. 08/384,240, which is a Continuation of application Ser. No. 08/143,480, now abandoned.

FIELD OF THE INVENTION

The present invention is directed generally to an apparatus for the detection of fluorescently labeled nucleic acids such as DNA and RNA which are separated by electrophoretic means. The present invention is particularly directed to an apparatus for scanning across an electrophoretic separation device and simultaneously collecting data from multiple fluorophores for application to DNA mapping, sequencing, or other uses.

DESCRIPTION OF THE PRIOR ART

Electrophoresis is the movement of charged molecules in an electric field. It is an important method for the separation of biological molecules because it usually does not affect the native structure of biopolymers and because it is highly sensitive to small differences in both charge and mass. Electrophoresis through agarose or polyacrylamide gels is the standard method used to separate and identify nucleic acid fragments, especially ribonucleic acid (RNA) and deoxyribonucleic acid (DNA) fragments. Detection of nucleic acid fragments is accomplished either in real-time during electrophoresis (known as on-line detection) or after electrophoretic separation has occurred (known as off-line detection) by use of highly sensitive visualization techniques. These techniques must necessarily have high sensitivity because each fragment is present in minute amounts. For conventional detection methods relying on labeling the molecules with a radioactive marker, the most common means of visualization is exposure to x-ray film after the electrophoretic separation. Detection by autoradiography of $^{32}$P-labeled nucleotides is presently the most common method of visualizing the separated nucleic acid fragments.

The prior art also describes the use of fluorescent labels for detection. Oligonucleotide primers containing fluorescent groups have been synthesized and can be used in place of radioisotopes for sensitive detection of nucleic acid fragments in primed synthesis such as the polymerase chain reaction amplification of DNA, or in DNA sequencing. These modified primers are highly fluorescent, are suitable for hybridization with specific DNA sequences, and do not adversely affect the electrophoretic separation of DNA molecules in polyacrylamide gels.

Detection of the fluorescent labels can be accomplished by directing a laser of the appropriate excitation wavelength upon the gel. The fluorescent light emitted from the fluorophores is collected and focused onto an appropriate detector. If a plurality of fluorescent dyes are used to label the DNA, filters which select a particular wavelength constituent from the fluorescent emissions are positioned in front of the detectors. In the case of DNA mapping, the size of fragments can be deduced by co-electrophoresis of a standard set of fragments of known length with the unknown samples. For DNA sequencing, the elution order of fluorescently-labeled DNA fragments determines the sequence of the DNA fragment being studied, either by labeling the DNA with a number of distinct fluorophores and eluting these fragments in the same lane, or by eluting the different nucleotide reactions in separate lanes on the gel, or by a combination of both methods. Examples of prior art devices follow.

U.S. Pat. No. 5,091,652 to Mathies et al. describes an off-line (post-separation) method wherein the entire gel is scanned using a short depth of focus confocal fluorescence detection system. The use of only a single fluorophore is described. While off-line detection methods such as that of Mathies et al. allow detection to be carried out independently of the electrophoretic separation, the additional processing of the gel that is necessary after separation makes off-line of detection methods more time consuming and less cost-effective than other methods.

In contrast, on-line detection schemes allow detection of the fluorescent labels to be accomplished during the process of electrophoresis to obtain the time-resolved emissions of the different fluorophores as the molecules pass by the detector region. Because on-line detection is faster than off-line detection, it is more widely used. Descriptions of several real-time on-line fluorescence detectors are provided in U.S. Pat. Nos. 4,811,218 to Hunkapiller et al., 5,062,942 to Kambara, 4,881,812 to Ohkubo et al., and 4,729,947 to Middendorf. In these patents, two types of signal detection are demonstrated in conjunction with on-line detection: single fluorophore and multiple fluorophore. The former type is described by Okhubo et al., and the latter is described by Hunkapiller et al., Kambara, and Middendorf.

Of these on-line analyzers, those that use multiple fluorophore detection systems have superior sample throughput. The single fluorophore detectors have limited throughput simply because the number of samples that can be loaded on the gel is reduced by up to a factor of four when compared to the multiple fluorophore approach described by Hunkapiller et al. Although single fluorophore detection instruments tend to be less complicated in design and are thus generally less expensive, the reduction in throughput is not compatible with the desire for the most rapid DNA analysis possible.

The multiple fluorophore detectors are categorized into two types. The first type of multiple fluorophore detection scheme employs a scanning detection stage with a moving filter wheel such that only one fluorophore is detected for every scan across the gel (Hunkapiller et al., supra.). This requires that for a plurality of four fluorophores, four scans of the entire gel width must be completed to collect the data for one duty cycle. This type of detector also fails to satisfy the need for high speed DNA analysis.

The second type of multiple fluorophore detection scheme utilizes a stationary laser beam introduced through the side of the gel and a prism and filter assembly to image the four wavelengths onto a two dimensional array detector (Kambara, supra.). Although this detection scheme has advantages in that it does not have moving parts and fluorescence detection of multiple samples can proceed rapidly due to the imaging strategy, the nature of Gaussian beam optics limits the ability to focus a laser beam reliably into the ultrathin gels currently favored in the art. Furthermore, the optical design employed places stringent demands on the gel apparatus and separation medium. Subtle changes in the refractive index of the separation medium and the angle of entry of the excitation beam can have dramatic effects on how well the excitation beam remains in focus across the separation medium as well as how it aligns with the stationary photodetectors. In addition, microimperfections in the separation medium such as dust or air bubbles can have far-reaching effects by impairing beam quality downstream. These effects are minimized by the use of a scanning excitation light source. Additionally, the detection system used is complicated in design and expensive to construct. Therefore, to achieve the most efficient detection capability, a scanning detector which does not utilize costly optical and detection components is preferred.

While the prior art discussed above functions much more rapidly than the art of a decade ago, there is still a need for DNA analysis which is even more rapid. As an example, one of the major needs associated with the current international effort to map and sequence the approximately three billion bases of DNA contained within the human genome is the development of automated instrumentation to increase both the speed and reliability of current methods of DNA separation and detection. At present, the throughput of automated DNA analysis instruments is inadequate given the enormous scale of the human genome.

The art has responded to this need for greater analysis speed in fields outside that of automated mapping. Recent advances in gel electrophoresis have occurred which now make it possible to sequence and map nucleic acid samples roughly an order of magnitude faster than commonly used methodologies. The major advance associated with these developments is the ability to apply higher electric fields to the electrophoretic medium without deleterious thermal effects. This is due to the use of ultrathin capillary gels or ultrathin slab gels (Brumley and Smith, 1990, Nucleic Acids Research, 19:4121-4126) which are typically between 50 and 100 microns thick. The thinness of these gels allows electric fields as high as 400 V/cm to be applied across the gel without significant Joule heating. The increased applied field results in separations that require less than an hour of electrophoresis, whereas commonly available commercial devices need up to fourteen hours for separation.

However, while the development of ultrathin gel electrophoresis systems is a significant breakthrough in increasing the rate of DNA analysis, it places stringent demands on the automated on-line fluorescence detection systems of the prior art. At present, the prior art detection sensitivity and detection rate are unsuitable for use with ultrathin gels for two reasons. First, prior art detection systems do not have the sensitivity necessary to accurately detect the smaller amounts of DNA that are loaded onto these ultrathin gels, which utilize as little as one-third of the genetic material utilized in the thicker gel slabs or columns of the prior art. Second, insofar as on-line detection is concerned, the detection of fluorophores must occur at a rate as rapid as the rate of electrophoresis. Since capillary electrophoresis and Horizontal Ultrathin Gel Electrophoresis occur at high speed, the prior art does not yet include a detection apparatus or method which detects fluorophores rapidly enough for use with these electrophoresis methods. The development of an instrument which combines the advantages of an improved separation method (such as the use of ultrathin gels) and high sensitivity detection is important for significantly increasing the throughput of DNA analysis and ensuring the success of projects such as the Human Genome Initiative.

SUMMARY OF THE INVENTION

It is an object of this invention to provide a high-speed, high-sensitivity fluorescence detection system suitable for use with ultrathin gels.

It is also an object of this invention to detect fluorescent emissions from multiple fluorophores simultaneously in a plurality of defined lanes or separation channels (e.g. capillaries) during electrophoretic separation.

It is another object of the invention to excite the fluorescent dyes that are used in labeling and also to collect their fluorescent light emissions to obtain the highest signal to noise ratio.

It is another object of the invention to minimize the cost and complexity of the fluorescent detection apparatus while providing high sensitivity, resolution, and sample throughput.

It is another object of the invention to maximize the light collected simultaneously from a number of fluorophores and distributed to a number of detectors with a minimum of light loss.

It is another object of the invention to resolve the plurality of fluorophores used by spectral analysis means, rather than to resolve them through the use of mechanical means (e.g., the mechanical switching of filters).

These objects and others are fulfilled by an apparatus for scanning an electrophoretic separation medium containing labeled molecules comprising excitation means for generating excitation light capable of generating a signal from the labeled molecules; scanning means for scanning the excitation light across the separation medium; a dichroic mirror array aligned to receive the signal from the labeled molecules, the dichroic mirror array including a plurality of dichroic mirrors arranged in succession, each dichroic mirror having distinct filtering characteristics wherein the signal is separated into distinct wavelength constituents by reflection at predetermined wavelengths and transmission at other wavelengths; and a plurality of detectors, each detector receiving a distinct wavelength constituent from one of the dichroic mirrors.

In addition, these objects are achieved by an apparatus for scanning an electrophoretic separation medium containing molecules labeled with fluorophores comprising excitation means for generating excitation light capable of generating fluorescent emission from the fluorophores, the fluorescent emission including distinct wavelength constituents; a first light guide for receiving the excitation light from the excitation means and transmitting the excitation light away from the excitation means; a scanning means for receiving the excitation light from the first light guide and focusing the excitation light onto the electrophoretic separation medium, scanning the excitation light across the plurality of distinct lanes, and collecting the fluorescent emission from the fluorophores; a second light guide for receiving the fluorescent emission from the scanning means and transmitting the fluorescent emission away from the scanning means; a plurality of dichroic mirrors arranged in succession, each dichroic mirror having filtering characteristics wherein incident fluorescent emission is separated into the distinct wavelength constituents by reflection at predetermined wavelengths and transmission at other wavelengths, wherein each dichroic mirror is aligned to receive at least one distinct wavelength constituent; and a plurality of detectors, each detector being aligned to receive at least one distinct wavelength constituent from a dichroic mirror.

Further, these objects are achieved by an apparatus for scanning an electrophoretic separation medium containing molecules labeled with fluorophores, the apparatus comprising excitation means for generating excitation light; a first fiber optic cable for receiving the excitation light from the excitation means; a focusing lens which receives the excitation light from the first fiber optic cable at a location remote from the excitation means and focuses the excitation light upon the electrophoretic separation medium, thereby causing the fluorophores in the separation medium to generate a fluorescent emission which includes distinct wavelength constituents; a collection lens which receives and focuses the fluorescent emission; a second fiber optic cable for receiving the fluorescent emission from the collection lens; a dichroic mirror array aligned to receive fluorescent emission from the second fiber optic cable, the dichroic mirror array including a plurality of dichroic mirrors aligned in succession, wherein each dichroic mirror has filtering characteristics allowing separation of the fluorescent emission into distinct wavelength constituents by reflection at predetermined wavelengths and transmission at other wavelengths, and further wherein each dichroic mirror is aligned to receive at least one distinct wavelength constituent; a plurality of detectors, each detector being aligned to receive at least one distinct wavelength constituent from a dichroic mirror; and a linear translator upon which the focusing lens and collection lens are mounted, the linear translator being adapted to translate across the electrophoretic separation medium.

A fluorescence detection apparatus has been developed which scans across an electrophoretic separation medium and detects multiple fluorophores present in the medium rapidly and simultaneously. First, the light from an appropriate light source is transmitted to the electrophoretic separation medium by a lightweight, flexible light guide. The fluorescently-labeled molecules in the separation medium are thereby excited with the excitation light in such a way that scattered background light is minimized. The resulting emitted fluorescence is collected by a lightweight, flexible light guide (which can be integral with the first light guide) and directed by an array of dichroic mirrors into multiple photodetectors. Each dichroic mirror only allows certain wavelength constituents of the fluorescent light (i.e., certain wavelength bands or colors) to be reflected to a photodetector, while all remaining light is transmitted to other dichroic mirrors in the array. Alternatively, certain wavelength constituents can be transmitted to photodetectors and the remaining wavelengths may be reflected to other dichroic mirrors in the array. The dichroic mirror array allows the different wavelength constituents of the fluorescent light to be simultaneously resolved and detected while minimizing light loss due to absorption and reflection, such as the light loss which occurs with the use of filters. Additionally, use of the lightweight, flexible light guides allows their affixment to and use on equipment which scans the electrophoretic separation media at extremely high speeds.

The general purpose of the invention is to automate the process of DNA sequencing, mapping, and fragment detection in electrophoretic separation media and increase the speed of such separation and detection to a level heretofore unknown in the art. In particular, the purpose of the invention is to provide an automatic DNA detection apparatus for use with polyacrylamide ultrathin gels, which cannot be automatically analyzed by the methods and apparatuses of the prior art. The apparatus provides a means to rapidly, inexpensively, and with high sensitivity, separate and detect DNA fragments by use of a lightweight, fast scanning mechanism and highly efficient collection optics which can simultaneously detect multiple wavelengths. There are several improvements to existing automated DNA sequencing systems that this apparatus addresses, including:

Cost: this apparatus uses readily available components that are relatively inexpensive, easy to assemble, reliable and fast. This significantly reduces the cost of this instrument when compared to other commercially available systems.

Efficiency: this apparatus utilizes a dichroic mirror array in tandem with several photodetectors to simultaneously detect a plurality of fluorophores with a minimum in light loss due to reflection, absorption or attenuation. The emitted fluorescence is simultaneously collected from a plurality of fluorogenic compounds, and the spectra are simultaneously divided and directed to a corresponding plurality of photodetectors in a single scan. The single scan eliminates the time loss inherent in the devices of the prior art, which need multiple scans or complex and expensive switching equipment to resolve multiple dyes.

Sensitivity: the invention has a higher sensitivity per unit of sample being analyzed than currently available systems because it uses ultrathin gels combined with automated fluorescence detection. Further, the dichroic mirror array used to collect the emitted light from the fluorophores and distribute it to multiple detectors has practically no light loss, and therefore sensitivity is not sacrificed for the sake of speed or efficiency.

Speed: The apparatus works faster than prior art inventions because multiple fluorophores are detected simultaneously and also because a lightweight scanning arrangement allows faster scanning. The invention provides a speed gain of 7–10 times the throughput (measured in nucleotide bases per hour) of currently available commercial instruments.

Further objects, features and advantages of the present invention will be apparent from the following detailed description, drawings and claims.

DESCRIPTION OF THE DRAWINGS

FIG. 9 is a schematic view of a third alternate embodiment of the scanning stage of the electrophoresis analyzer of FIG. 1.

FIG. 10 is a cutaway view of the light guide of FIG. 9 as viewed from the cutaway line 10—10 in FIG. 9.

DETAILED DESCRIPTION OF THE INVENTION

Figure 1:
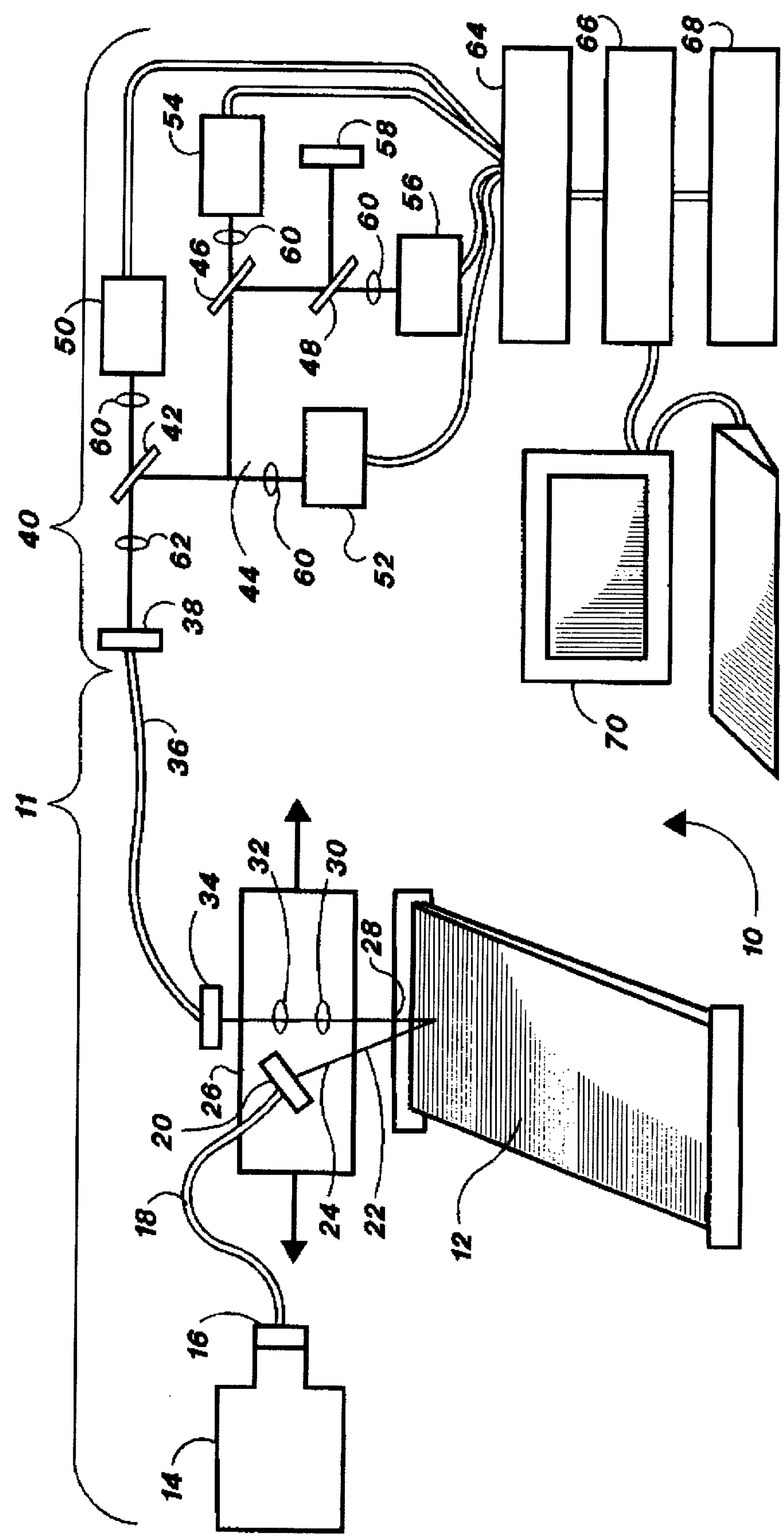
FIG. 1 is a schematic view of the electrophoresis analyzer apparatus of the present invention.

Referring now to the figures in which the same reference numbers are given to the same or similar structures throughout the several drawings, FIG. 1 schematically illustrates one embodiment of the analyzer 10. The main components of the analyzer 10 are a scanning stage 11, which rests above a gel separation medium 12, and a dichroic mirror array 40. The gel separation medium 12 contains fluorophore-labeled nucleic acids which are being separated as the analyzer 10 operates, and is preferably of the ultrathin variety, including but not limited to a horizontal ultrathin gel apparatus or an array of gel-filled capillaries.

The scanning stage 11 includes a laser 14 which operates in multiline mode. Light from the laser 14 is directed into the input end 16 of a first light guide 18. This light guide 18 is preferably a fiber optic cable which preserves the polarization of the transmitted light, such as the PMJ series fiber optic cables available from Oz Optics Inc., Carp, Ontario, Canada, which maintain polarization to 25 dB. The first light guide 18 transmits the laser light to its output end 20. As .electrophoresis occurs, the laser light 22 from the output end 20 is focused through a low numerical aperture focal lens 24 onto the gel slab separation medium 12 at Brewster's angle. The focal lens 24 focuses the excitation light 22 exiting from the output end 20 of the first light guide 18 to a spot size on the order of 100 microns. The incident excitation light 22 causes the fluorophores in the gel separation medium 12 to fluoresce at the characteristic wavelength of the fluorophores. The emitted fluorescence signal 28 is collected by a high numerical aperture collection lens 30 (e.g., the #78776 Nikon 40X Achromat microscope objective with 0.5 N.A. and 10.1 mm working distance, from Nikon Inc., Melville, N.Y.) and focused onto the input end 34 of a second light guide 36 (i.e., a fiber optic cable), preferably by use of an f/2 lens 32 (e.g., the PAC022 f/2 Achromat lens available from Newport Corp., Irvine, Calif.).

A scanning means for scanning the excitation light 22 across the gel slab 12 is provided. The output end 20 of the first light guide 18 and the lens 24, as well as the lenses 30 and 32 and input end 34 of the second light guide 36, are attached to a linear translator (shown schematically at 26). The linear translator 26 is driven by motors to allow the incident light 22 (and emitted light signal 28) to scan back and forth across the gel slab 12 in a direction perpendicular to that of the electrophoresis as the electrophoretic separation proceeds.

To aid in focusing the laser light 22 onto the gel slab separation medium 12, the focal lens 24 and collection lens 30 are attached to the linear translator 26 by means of mounts (not shown) that allow proper focusing of the focal lens 24 and the collection lens 30. An example of such a mount is a microscope body mount which has an adjustment knob to allow proper focusing of the laser light 22 onto the gel slab separation medium 12.

The second light guide 36 transmits the fluorescent signal 28 to its output end 38, where the fluorescent signal 28 is directed out of the scanning stage 11 and into an array of dichroic mirrors 40. Each dichroic mirror 42, 44, 46, and 48 is specially selected to reflect only selected wavelengths to its respective photodetector 50, 52, 54, and 56, and transmit the remaining light to the other dichroic mirrors or to a beamstop 58. As an example, the dichroic mirrors can have bandpass characteristics: the first dichroic mirror 42 can transmit all light at 610±10 nm (effectively reflecting all light below 600 nm and above 620 nm); the second dichroic mirror 44 can transmit all light at 580±10 nm (effectively reflecting all light below 570 nm); the third dichroic mirror 46 can transmit all light at 560 nm+10 nm (effectively reflecting all light below 550 nm); the fourth dichroic mirror 48 can transmit all light at 540 nm±10 nm (effectively reflecting all light below 530 nm); and the remaining light is directed to and absorbed by the beamstop 58. Alternatively, the dichroic mirrors can have high-pass characteristics, wherein all wavelengths above a cutoff wavelength are transmitted through the mirrors and all wavelengths below cutoff are reflected, or low-pass characteristics, wherein all wavelengths below a cutoff wavelength are transmitted through the mirrors and all wavelengths above cutoff are reflected. Dichroic mirrors such as the ones described above can be obtained from Omega Optical, Brattleboro, Vt. Each photodetector 50, 52, 54, and 56 is intended to detect fluorescence in the wavelength region in which a particular dye emits light. While four dichroic mirrors and photodetectors are shown, the fluorescent light may be split into as many wavelength regions as there are dyes to detect.

Achromat lenses 62 and 60 may be employed in the dichroic array 40 to first collimate the emergent fluorescence from the light guide 36 and then focus the fluorescence onto the photodetectors 50, 52, 53, and 56. For example, a f/2 achromat lens 62 (e.g., the PAC022 lens from Newport Corp., Irvine, Calif.) positioned one focal length away from the output end of the light guide 38 will collimate the emergent fluorescent signal 28. This light is then focused onto the photodetectors using an achromat lens 60 (e.g., the f/1.5 PAC019 lens available from Newport, Irvine, Calif.) which is interposed between each dichroic mirror 42, 44, 46, and 48 and their respective photodetectors 50, 52, 54, and 56 so that the wavelength constituents of the fluorescent signal 28 may be focused onto the photodetectors. Alternatively, the achromat lenses 60 in front of the photodetectors may be removed and the front achromat lens replaced with a lower f/# achromat (e.g. an f/1.5 PAC019 lens available from Newport Corp., Irvine, Calif.) which will allow the fluorescent signal 28 emerging from the output end of the light guide 38 to be focused directly onto the photodetectors 50, 52, 54, and 56, provided all photodetectors are the same distance away from the achromat lens 62. The latter method is used in the preferred embodiment of the analyzer 10.

The photodetectors 50, 52, 54, and 56 may themselves be mounted to translation stages or other means which allow fine adjustment of the height and position of the photosensitive surface of the photodetectors relative to the focused fluorescence. The photodetector housings are shielded and are provided with the appropriate voltage supply.

The output of each photodetector is integrated over each sample period and sent to a preamplifier 64. The preamplifier 64 provides an amplified voltage output and applies low pass filtering to the signal at a user-defined cutoff frequency between about 100 and 1000 Hz. This cutoff frequency is determined by the expected frequency of the fluorescence signal. For example, if fluorescence from 100 sample lanes were collected from a single scan in a period of 1 second, then depending on the spacing between lanes, the time-varying fluorescence from this scan should have a maximum frequency of approximately 100 Hz. Any fluorescence frequencies above 100 Hz would not be informative and would most likely be due to noise inherent in the photodetector or noise from scattered light. The voltage outputs from the preamplifier 64 are then sent to an analog to digital (A/D) converter 66. The A/D converter 66 takes readings approximately every millisecond and sends the values to a SCSI or I/O interface box 68, which in turn relays the values to a computer 70. Data collection is controlled by custom software which collects, displays, stores, and analyzes the raw data obtained from the analyzer 10.

In the embodiment discussed above, the carefully engineered use of fiber optics in the scanning stage 11 of the analyzer 10 reduces the weight of the linear translator 26 to such an extent that scanning speeds much greater than those of the prior art may be employed. In particular, the use of the flexible, lightweight first light guide 18 to transmit the excitation light to the gel slab 12 and the use of the light guide 36 to transmit the fluorescent signal 28 to the photodetectors 50, 52, 54, and 56 allows the laser 14 and photodetectors to be located remotely from the linear translator 26, allowing a decrease in the inertia of the linear translator 26 and a consequent increase in its scanning speed.

Additionally, the use of successive wavelength-selective dichroic mirrors allows simultaneous detection of multiple fluorophores in each scanning pass across the gel slab 12, and a consequent increase in speed when compared to the mechanical switching of filters illustrated in the prior art. The use of a dichroic mirror array 40 to resolve the collected fluorescence into component wavelengths additionally results in a highly efficient means to detect fluorescence from complex mixtures of fluorophores because there is no loss of information-bearing light from absorption by filters. Altogether, the higher scanning speeds and the simultaneous detection of multiple fluorophores allows the apparatus to operate at speeds of 7–10 times greater than the automated DNA analysis apparatus of the prior art.

Other means can be used to add further advantages to the analyzer 10. Ideally, the first light guide 18 of the embodiment of FIG. 1 preserves the polarization of the laser 14 in order to take full advantage of Brewster's angle, the angle at which the p-component of the excitation light 22 does not reflect off an interface (here, the air-glass interface at the gel slab separation medium 12). This yields the highest transmission through the glass into the separation medium 12 and reduces scattering. However, the analyzer 10 still works well if the first light guide 18 does not preserve the polarization. Two alternative embodiments are contemplated where a polarization-preserving first light guide 18 is not used. First, a conventional first light guide 18 may be used with a polarizer (e.g., a dichroic sheet polarizer such as the series 03-FPG available from Melles Griot, Irvine, Calif.) at the output end 20 to achieve the full benefit of the Brewster's angle strategy. However, a significant portion (approximately 68%) of the incident energy of the beam will be attenuated by such a polarizer. Thus, a second embodiment uses excitation without polarization of the incident beam 22. In this instance, a more inexpensive and readily available first light guide 10 may be used without any polarizing means, resulting in a modest reflection loss (approximately 15%) at the surface of the gel slab separation medium 12. In this situation, there is no significant advantage in using Brewster's angle over any other angle.

As noted above, the apparatus may use a Brewster's angle excitation strategy to direct the excitation light 22 into the gel slab separation medium 12. However, there are several other means detailed in the prior art that can be used to effectively send the excitation light into the separation medium. Common examples of these means are confocal excitation as described by Mathies et al. and through-medium excitation as described by Okhubo et al. The main criterion in all of these methods is maximizing sample illumination while minimizing illumination from the separation medium and radiation scattered from surface interfaces. Regardless of which excitation strategy is used, the signal to noise ratio is increased if the excitation light is focused to as small a spot size as possible considering the geometric constraints imposed by the separation method employed. The use of a light guide 18 (such as a fiber optic cable or bundle) to pipe excitation light to the separation medium 12 also helps to reduce interference created by scattered and stray light.

Figure 2:
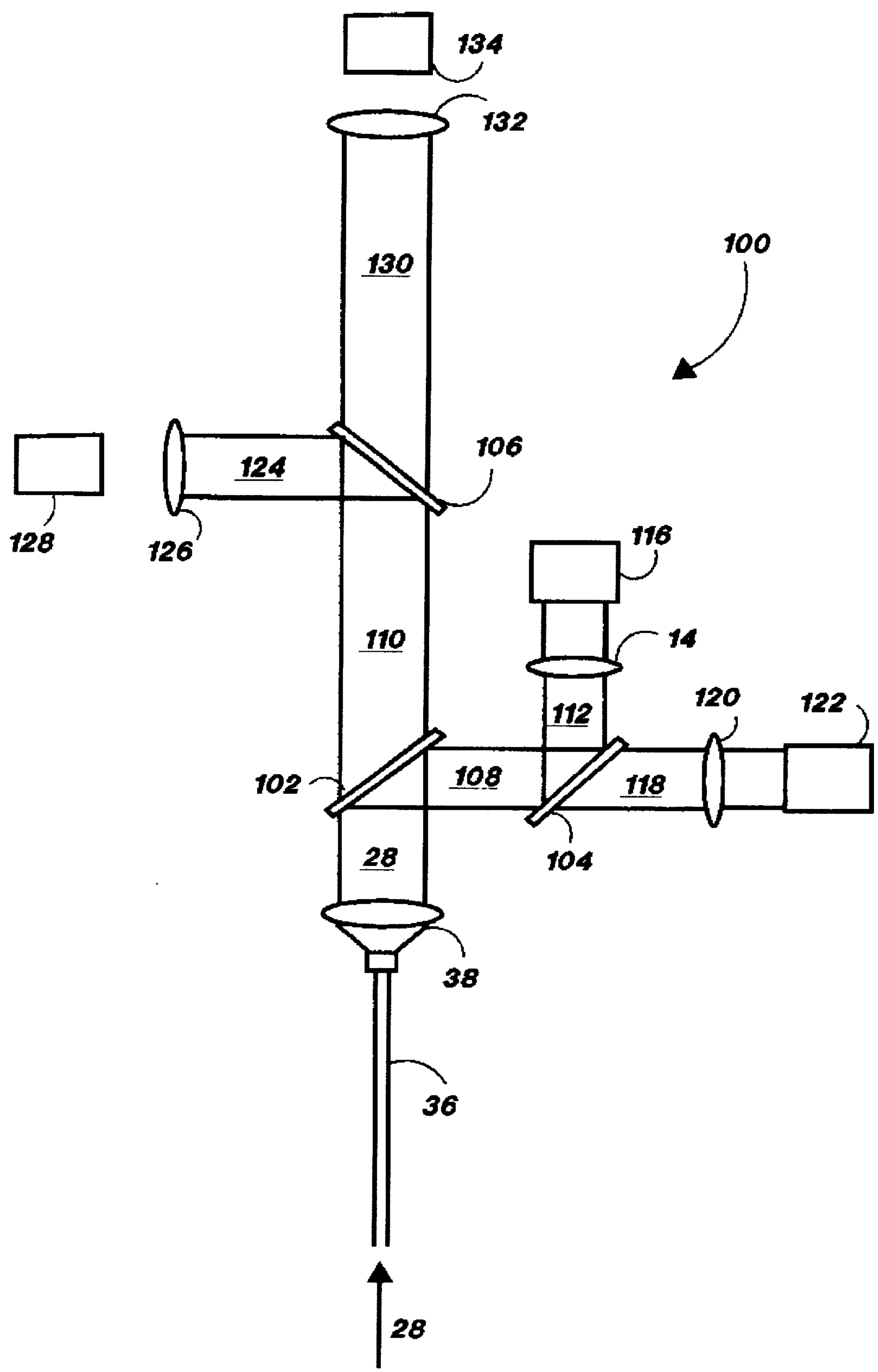
FIG. 2 is a schematic view of an alternate embodiment of the dichroic mirror array of FIG. 1.

The dichroic mirror array 40 may be arranged in several different ways and may contain different numbers of mirrors. As illustrated in FIG. 1, the dichroic mirrors 42, 44, 46, and 48 may be arrayed in succession in linear fashion, with each mirror transmitting the appropriate wavelengths to the detectors 50, 52, 54, and 56. An alternative array 100 with three dichroic mirrors 102, 104, and 106 is shown in FIG. 2 wherein the dichroic mirrors are aligned in nonlinear succession. In this array 100, a dichroic mirror 102 receives the fluorescent light signal 28 from the output end 38 of the second light guide 36 and simultaneously reflects certain wavelength constituents 108 to dichroic mirror 104 and transmits certain wavelength constituents 110 to dichroic mirror 106. The dichroic mirror 104 then reflects wavelength constituents 112 to achromat lens 114 and detector 116, and transmits wavelength constituents 118 to achromat lens 120 and detector 122. Similarly, the dichroic mirror 106 reflects wavelength constituents 124 to achromat lens 126 and detector 128 and transmits wavelength constituents 130 to achromat lens 132 and detector 134. No beamstop 58 is necessary, and less dichroic mirrors are used when compared to the embodiment of FIG. 1. In accordance with the principles taught by the first and second embodiments of the dichroic mirror array 40 and 100, the dichroic mirrors may be configured in several different ways to meet space or design requirements.

Figure 3:
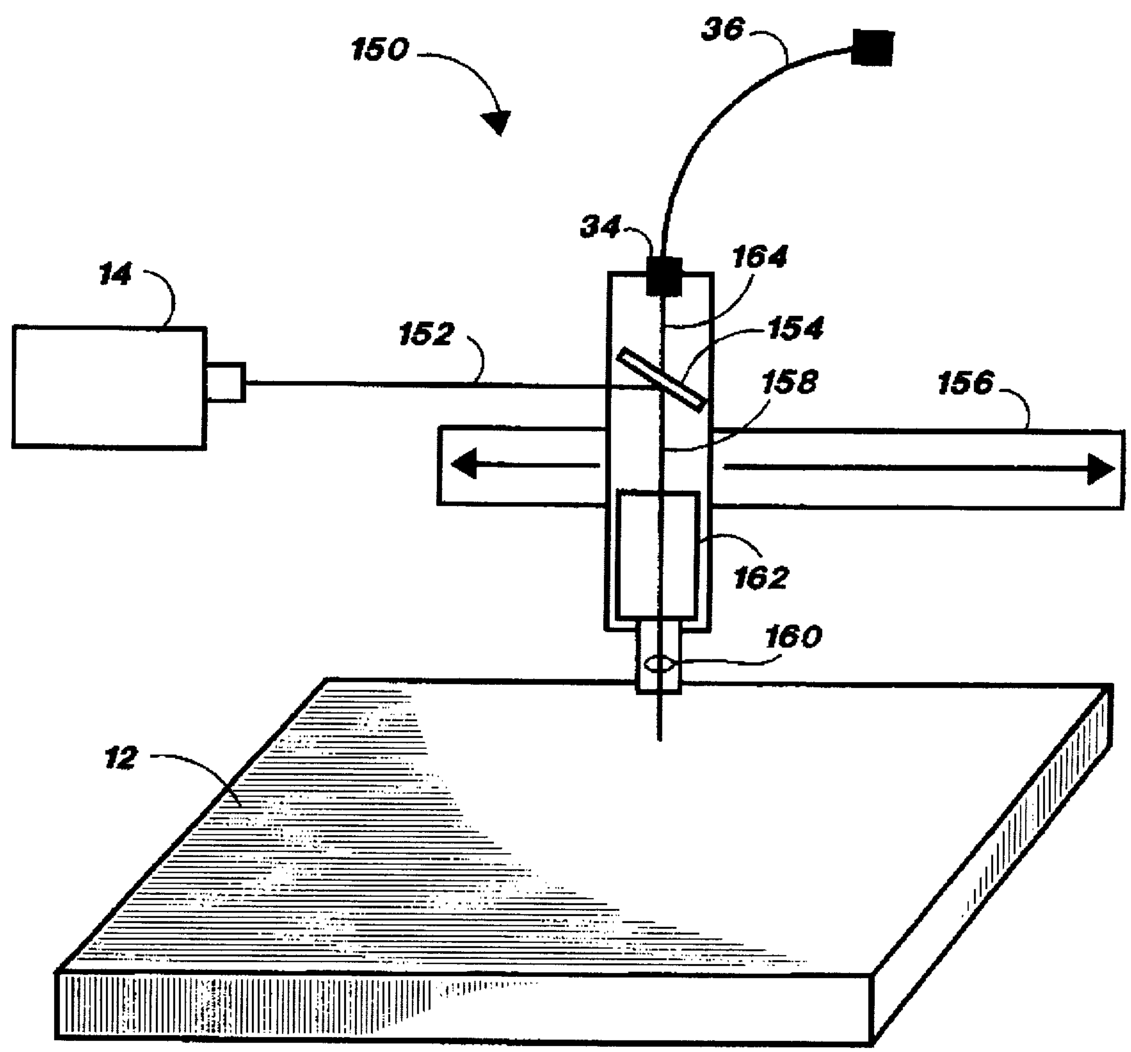
FIG. 3 is a schematic view of an alternate embodiment of the scanning stage of the electrophoresis analyzer of FIG. 1.

FIG. 3 is a schematic diagram illustrating another embodiment of the scanning sturge 11 of the analyzer 10. This scanning stage 150 utilizes a confocal strategy to direct the excitation light 152 from the laser 14 into the separation medium 12. The excitation light 152 is first directed above the plane of the gel separation medium 12. If desired, beam steering mirrors, galvanomirrors, or a light guide may be used to orient the beam as desired. The laser light 152 is then reflected downward toward the separation medium gel slab 12 using a dichroic mirror 154 mounted on a linear translator 156. The dichroic mirror 154 reflects light about the wavelength band of the incident laser light 152 and transmits all other wavelength constituents within the light 152. As an example, if the dichroic mirror 154 is to be used with an argon laser, the dichroic mirror 154 should reflect light between 470 and 520 nm. The reflected laser light 158 is then passed through a high numerical aperture objective lens 160 mounted within a microscope objective 162 which preferably has an adjustment knob (not shown) to allow proper focusing of the laser light 158 onto the gel slab 12. The objective lens 160 focuses the laser light 158 to a spot size on the order of 10 microns. The emitted fluorescence 164 is collected by the same objective 160 used to focus the laser light 158 onto the gel slab 12. This fluorescence 164 passes through the dichroic mirror 154 and is directed into the input end 34 of fiber optic cable 36, where it is then transmitted to a dichroic mirror array and detector scheme such as that illustrated in either of FIGS. 1 or 2.

Figure 5:
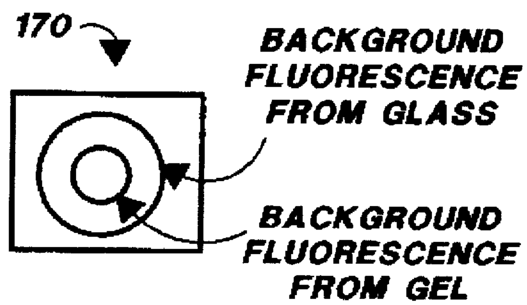
FIG. 5 is a view of the image produced by the focusing and collection optics of FIG. 4.
Figure 4:
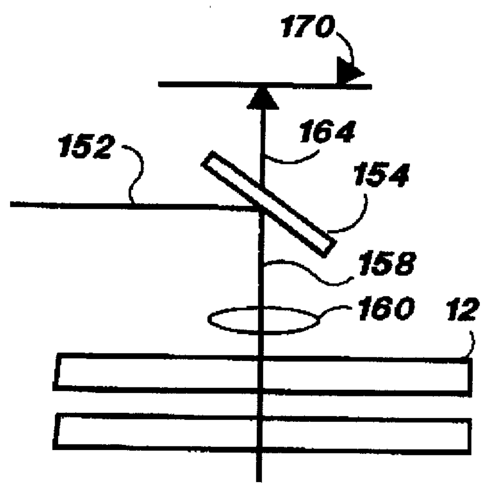
FIG. 4 is a schematic view of one embodiment of the focusing and collection optics utilizable in the scanning stage of FIG. 3.
Figure 6:
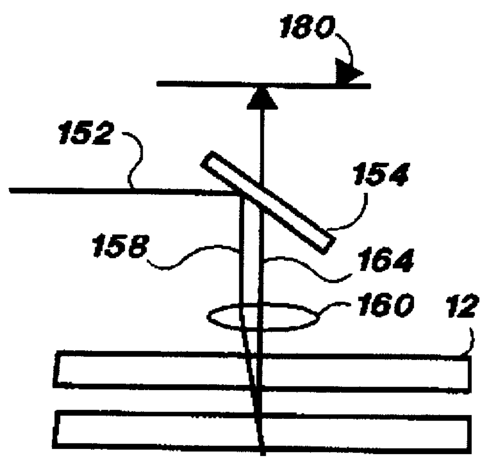
FIG. 6 is a schematic view of a second embodiment of the focusing and collection optics utilizable in the scanning stage of FIG. 3.
Figure 7:
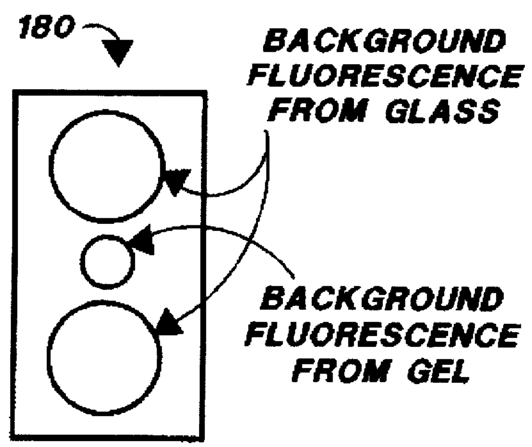
FIG. 7 is a view of the image produced by the focusing and collection optics of FIG. 6.

In the confocal arrangement of FIG. 3, the incident laser light 158 can be aligned to pass either directly through the center of the objective lens 160, as illustrated in FIG. 4, or slightly off center, as illustrated in FIG. 6. The arrangement illustrated in FIG. 4 is confocal where the incident light 158, emitted fluorescent light 164, and any scattered excitation light from the glass plates in the gel slab 12 are collinear. Such an arrangement results in the image 170 shown in FIG. 5, wherein the scattered light from the, glass-air interface is superimposed on the emitted fluorescence. The alternate arrangement illustrated in FIG. 6 directs the incident laser light 158 off-center from the focusing objective 160. This allows a degree of separation between the scattered excitation light and the emitted fluorescent light 164 that one wishes to collect, providing an image 180 as shown in FIG.

7. An off-axis arrangement thus allows the emitted fluorescent light 164 to be captured by the second light guide 36 while excluding scattered light and increasing the signal-to-noise ratio, provided the spatial separation between the emitted fluorescent light 164 and the adjacent scattered light is larger than the radius of the second light guide 36.

Confocal arrangements of the apparatus have the advantage that they are simpler and that the scanning stage tends to be of lighter weight, thereby allowing a further increase in scanning speed. However, arrangements such as those shown in FIG. 1, where the focal and collection lenses are separate, have the advantage that the focusing of the laser is independent of the collection of the fluorescent emitted light and the spot size of the laser may be independently adjusted. One skilled in the art can choose the configuration that best suits his or her needs.

Figure 8:
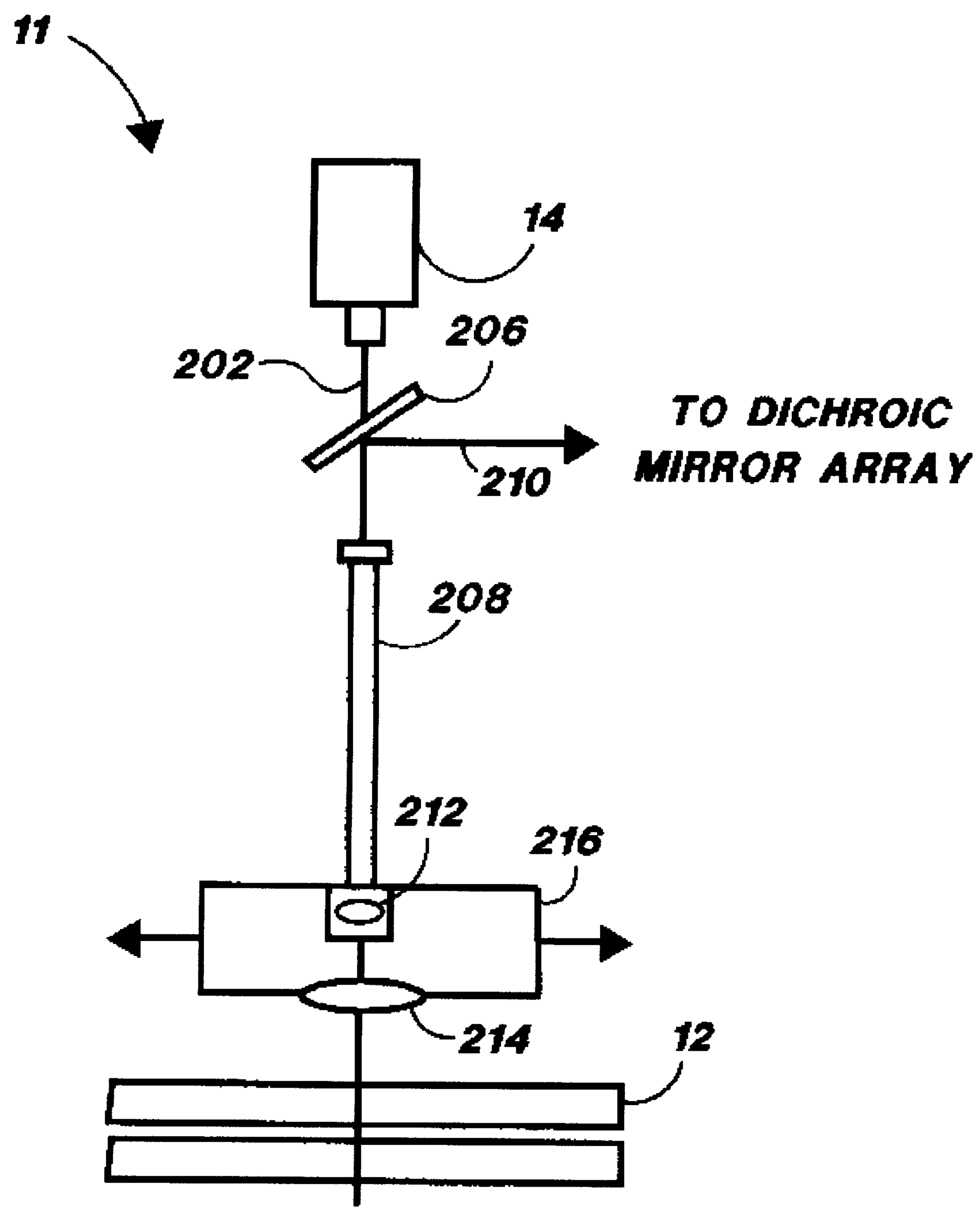
FIG. 8 is a schematic view of a second alternate embodiment of the scanning stage of the electrophoresis analyzer of FIG. 1.

As FIGS. 3–6 illustrate, there are several different ways to direct the excitation light 158 into the gel slab separation medium 12. FIG. 8 is a schematic diagram illustrating yet another embodiment of the scanning stage 11 which uses a single light guide 200 to transmit light 202 from the laser 14 into the gel slab 12 and transmit emitted fluorescent light 204 from the gel slab 12 to a dichroic mirror array (not shown). A dichroic mirror 206 is used to separate the laser light 202 input to the light guide 208 from the fluorescent light 210 emitted by the gel slab 12. An objective lens 212 is used to focus the light and collimating lens 214 is provided to collimate the fluorescent light 210, which is then sent to a dichroic mirror array and detector arrangement. A linear translator 216 scans the objective lens 212 and collimating lens 214 across the gel slab 12 as electrophoresis occurs.

In a different embodiment, illustrated in FIGS. 9 and 10, the light guide 220 has an illumination bundle 222 that surrounds a collection bundle 224. The incident laser light 202 passes through the illumination bundle 222 and is focused onto the gel slab 12. The same light guide 220 will collect any emitted fluorescence from the gel slab 12 and direct this light through the collection bundle 224 to the dichroic mirror array and photodetectors.

Figure 11:
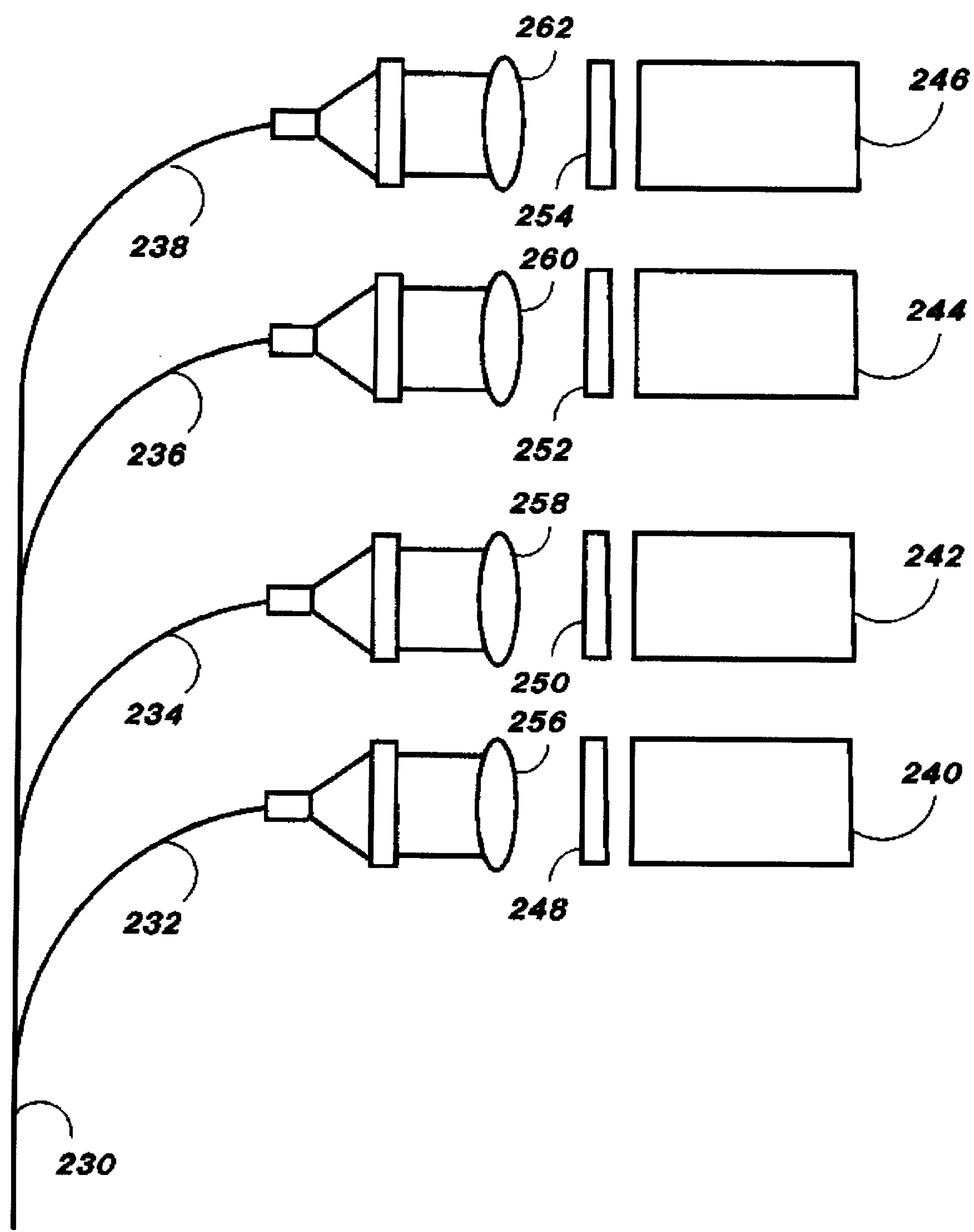
FIG. 11 is a schematic view of an alternate embodiment of the second light guide and the detection stage of FIG. 1.

In another embodiment, the general features of a scanning stage such as that shown in FIGS. 1, 3, 4, 6, and 8 are retained, but the collected fluorescence 210 is transmitted in a second light guide 230 which splits into multiple branches 232, 234, 236, and 238 and to multiple photodetectors 240, 242, 244, and 246 as illustrated in FIG. 11. The fluorescence is split imo as many pans as there are different fluorophores to detect. Wavelength discrimination can then be performed by placing one of several different bandpass filters 248, 250, 252, 254 between the collimating lenses 256, 258, 260, and 262 and the photodetectors. In this situation, each photodetector will receive a different wavelength band of the total collected fluorescence. However, because the intensity of the fluorescence is divided into the multiple branches, the signal strength to the photodetectors is diminished and sensitivity is decreased when compared to embodiments which use a dichroic mirror array, such as those shown in FIGS. 1 and 2. Additionally, light loss also occurs due to absorption from the filters. For this reason, embodiments such as those of FIGS. 1 and 2 are preferred.

It is noted that while the invention is particularly well suited for use with on-line analysis systems, wherein electrophoretic separation occurs concurrently with analysis, the invention may also be used with off-line analysis systems, wherein fluorophore detection and analysis occurs after electrophoretic separation occurs. In such a case, the linear translator is replaced with an x–y translation device.

It is understood that the invention is not confined to the particular construction and arrangement of parts herein illustrated and described, but embraces such modified forms thereof as come within the scope of the following claims.

We claim:

1. An apparatus for scanning an electrophoretic separation medium containing labeled molecules comprising:

a. excitation means for generating excitation light capable of generating a signal from the labeled molecules;

b. scanning means for scanning the excitation light across the separation medium;

c. a dichroic mirror array aligned to receive the signal from the labeled molecules, the dichroic mirror array including a plurality of dichroic mirrors arranged in succession, each dichroic mirror having distinct filtering characteristics wherein the signal is separated into distinct wavelength constituents by reflection at predetermined wavelengths and transmission at other wavelengths; and d. a plurality of detectors, each detector receiving a distinct wavelength constituent from one of the dichroic mirrors.

2. The apparatus of claim 1 further comprising a focusing lens connected to the scanning means for focusing the excitation light on the electrophoretic separation medium, and a collection lens connected to the scanning means for collecting the signal.

3. The apparatus of claim 2 wherein the focusing lens and the collection lens are integral.

4. The apparatus of claim 3 wherein the excitation light received by the focusing lens and the signal received by the collection lens are collinear.

5. The apparatus of claim 3 wherein the excitation light received by the focusing lens and the signal received by the collection lens are oblique.

6. The apparatus of claim 1 further comprising a first light guide for transmitting excitation light from the excitation means to the scanning means.

7. The apparatus of claim 6 wherein the first light guide comprises at least one fiber optic cable.

8. The apparatus of claim 6 wherein the first light guide further transmits the signal from the labeled molecules to the dichroic mirror array.

9. The apparatus of claim 6 wherein the first light guide comprises means for preserving the polarization of the transmitted excitation light.

10. The apparatus of claim 1 further comprising a second light guide for transmitting the signal from the electrophoretic separation medium to the dichroic mirror array.

11. The apparatus of claim 10 wherein the second light guide comprises at least one fiber optic cable leading from the scanning means to the dichroic mirror array.

12. The apparatus of claim 1 wherein the scanning means directs the excitation light to illuminate the labeled molecules at Brewster's angle.

13. The apparatus of claim 1 wherein the electrophoretic separation medium is a horizontal ultrathin gel.

14. The apparatus of claim 1 wherein the scanning means scans the separation medium simultaneously with electrophoretic separation in the separation medium.

15. The apparatus of claim 1 wherein the scanning means scans the separation medium after electrophoretic separation has been completed in the separation medium.

16. An apparatus for scanning an electrophoretic separation medium containing molecules labeled with fluorophores comprising:

a. excitation means for generating excitation light capable of generating fluorescent emission from the fluorophores, the fluorescent emission including distinct wavelength constituents;

b. a first light guide for receiving the excitation light from the excitation means and transmitting the excitation light away from the excitation means;

c. a scanning means for receiving the excitation light from the first light guide and focusing the excitation light onto the electrophoretic separation medium, scanning the excitation light across the plurality of distinct lanes, and collecting the fluorescent emission from the fluorophores;

d. a second light guide for receiving the fluorescent emission from the scanning means and transmitting the fluorescent emission away from the scanning means;

e. a plurality of dichroic mirrors arranged in succession, each dichroic mirror having filtering characteristics wherein incident fluorescent emission is separated into the distinct wavelength constituents by reflection at predetermined wavelengths and transmission at other wavelengths, wherein each dichroic mirror is aligned to receive at least one distinct wavelength constituent; and f. a plurality of detectors, each detector being aligned to receive at least one distinct wavelength constituent from a dichroic mirror.

17. The apparatus of claim 16 wherein the first light guide and second light guide comprise a single fiber optic cable.

18. The apparatus of claim 16 wherein the scanning means includes a focusing lens for focusing the excitation light from the first light guide onto the electrophoretic separation medium and a collection lens for collecting the fluorescent emission from the fluorophores.

19. The apparatus of claim 18 wherein the focusing lens and the collection lens are integral.

20. The apparatus of claim 19 wherein the focusing lens and the collection lens are adapted to provide a collinear confocal relationship between the excitation light and the fluorescent emission.

21. The apparatus of claim 19 wherein the focusing lens and the collection lens are adapted to provide an off-axis confocal relationship between the excitation light and the fluorescent emission.

22. An apparatus for scanning an electrophoretic separation medium containing molecules labeled with fluorophores, the apparatus comprising:

a. excitation means for generating excitation light;

b. a first fiber optic cable for receiving the excitation light from the excitation means;

c. a focusing lens which receives the excitation light from the first fiber optic cable at a location remote from the excitation means and focuses the excitation light upon the electrophoretic separation medium, thereby causing the fluorophores in the separation medium to generate a fluorescent emission which includes distinct wavelength constituents;

d. a collection lens which receives and focuses the fluorescent emission e. a second fiber optic cable for receiving the fluorescent emission from the collection lens;

f. a dichroic mirror array aligned to receive fluorescent emission from the second fiber optic cable, the dichroic mirror array including a plurality of dichroic mirrors aligned in succession, wherein each dichroic mirror has filtering characteristics allowing separation of the fluorescent emission into distinct wavelength constituents by reflection at predetermined wavelengths and transmission at other wavelengths, and further wherein each dichroic mirror is aligned to receive at least one distinct wavelength constituent;

g. a plurality of detectors, each detector being aligned to receive at least one distinct wavelength constituent from a dichroic mirror; and h. a linear translator upon which the focusing lens and collection lens are mounted, the linear translator being adapted to translate across the electrophoretic separation medium.

* * * * *

UNITED STATES PATENT AND TRADEMARK OFFICE
CERTIFICATE OF CORRECTION

PATENT NO : 5,538,613

DATED : July 23, 1996

INVENTOR(S) : Robert L. Brumley, John A. Luckey

It is certified that error appears in the above-identified patent and that said Letters Patent are hereby corrected as shown below:

Column 7, Line 61, delete "nm+10" and add -- nm $\pm$ 10 -- therefor.

Column 10, Line 26, delete "sturge" and add -- stage -- therefor.

Column 11, Line 47, delete "imo" and add -- into -- therefor.

Column 11, Line 47, delete "pans" and add -- parts -- therefor.

Signed and Sealed this

Tenth Day of March, 1998

Attest:

BRUCE LEHMAN

*Attesting Officer*

*Commissioner of Patents and Trademarks*